(12) United States Patent
Dunfee et al.

(10) Patent No.: US 7,527,636 B2
(45) Date of Patent: May 5, 2009

(54) INTRALUMINAL GUIDEWIRE WITH HYDRAULICALLY COLLAPSIBLE SELF-EXPANDING PROTECTION DEVICE

(75) Inventors: Albert H. Dunfee, Byfield, MA (US); David D. Barone, Lexington, MA (US)

(73) Assignee: Medtronic Vascular, Inc, Santa Rosa, CA (US)

( * ) Notice: Subject to any disclaimer, the term of this patent is extended or adjusted under 35 U.S.C. 154(b) by 784 days.

(21) Appl. No.: 10/713,503

(22) Filed: Nov. 14, 2003

(65) Prior Publication Data

US 2004/0153094 A1 Aug. 5, 2004

Related U.S. Application Data

(63) Continuation-in-part of application No. 10/295,153, filed on Nov. 14, 2002, now abandoned.

(51) Int. Cl.
*A61M 29/00* (2006.01)
(52) U.S. Cl. .................................................. 606/200
(58) Field of Classification Search ................ 606/113, 606/114, 127, 159, 200; 604/96.01; 623/1.11, 623/1.12, 1.13
See application file for complete search history.

(56) References Cited

U.S. PATENT DOCUMENTS

| 3,952,747 | A | * | 4/1976 | Kimmell, Jr. | ................ | 606/200 |
| 4,848,338 | A |   | 7/1989 | De Satnick et al. | | |
| 5,626,601 | A | * | 5/1997 | Gershony et al. | ........... | 606/194 |
| 5,814,064 | A |   | 9/1998 | Daniel et al. | | |

FOREIGN PATENT DOCUMENTS

EP 1 344 502 A2 9/2003

* cited by examiner

*Primary Examiner*—Kevin T Truong

(57) ABSTRACT

An intraluminal guidewire system comprises a first tubular member having a proximal end and a distal end and has a fluid containing lumen therethrough. A medical device is coupled to the first tubular member proximate the distal end. A slave actuating member is coupled to the medical device and is slidably mounted proximate the distal end for longitudinal movement with respect to the first tubular member. A master actuating member is configured for longitudinal movement within the first tubular member proximate the proximal end. The master actuating member is hydraulically coupled to the slave actuating member.

31 Claims, 6 Drawing Sheets

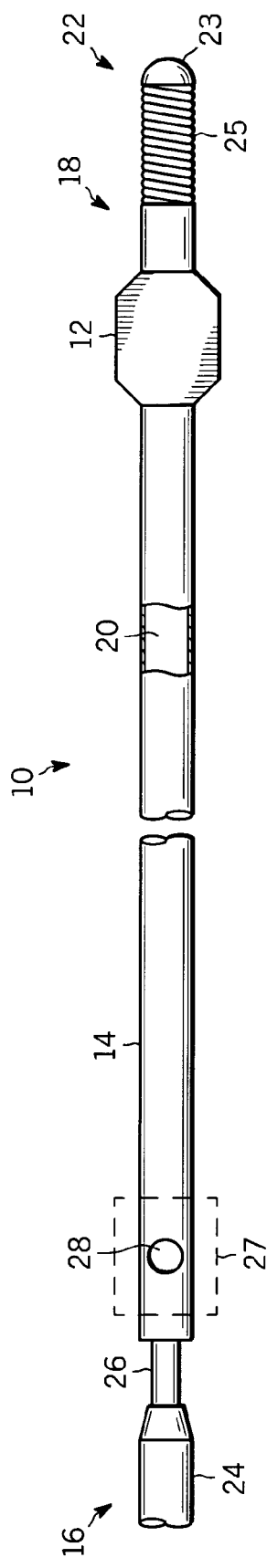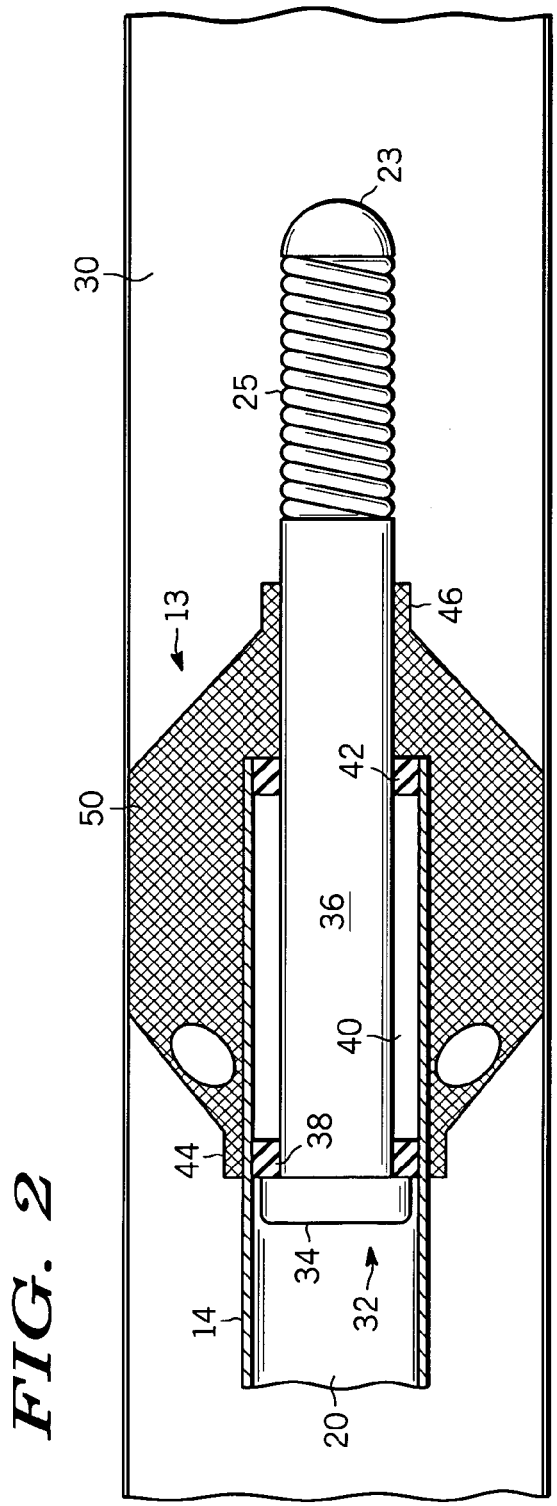

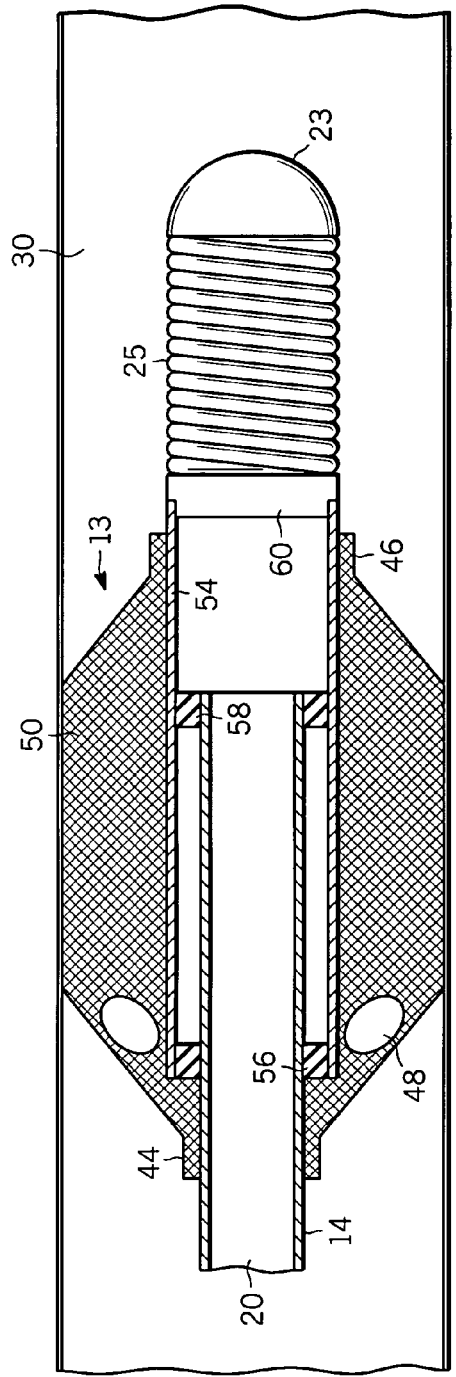
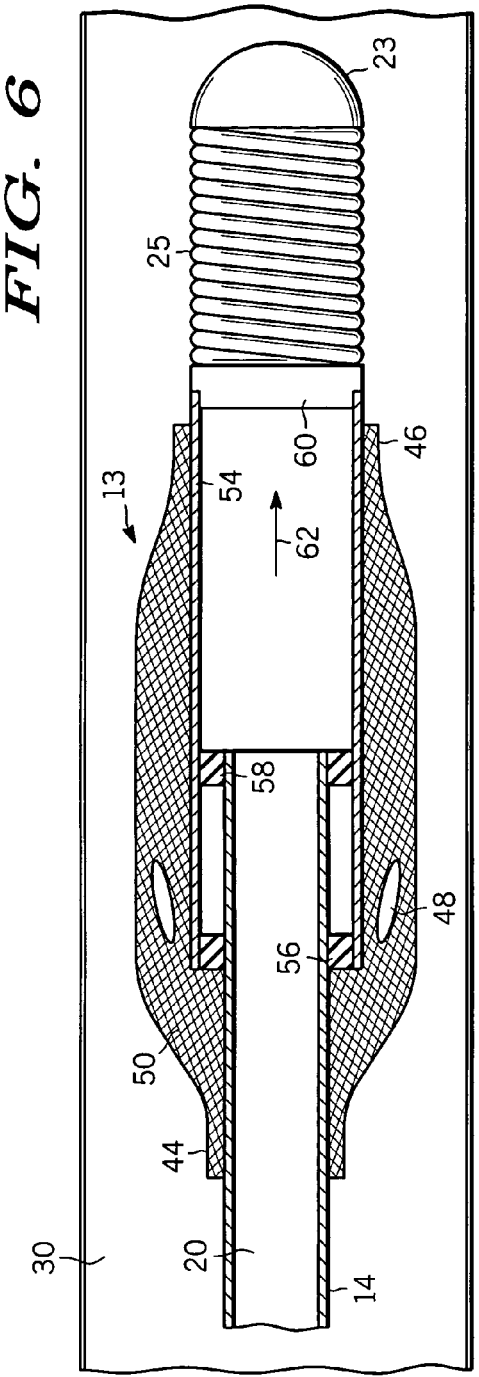
FIG. 5
FIG. 6

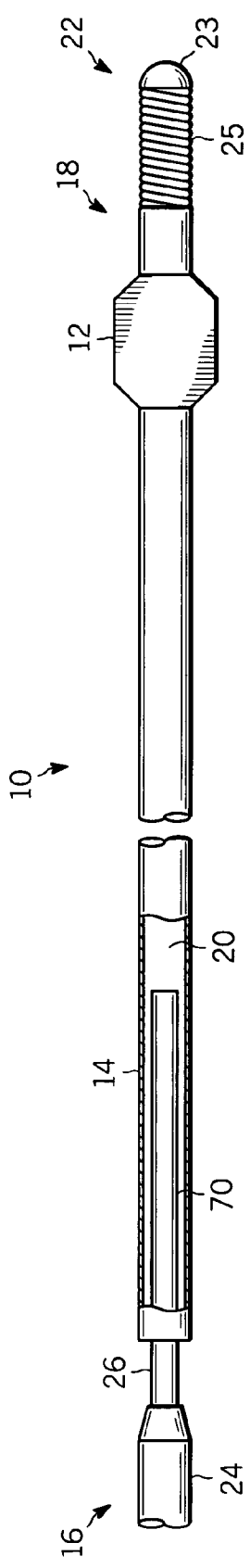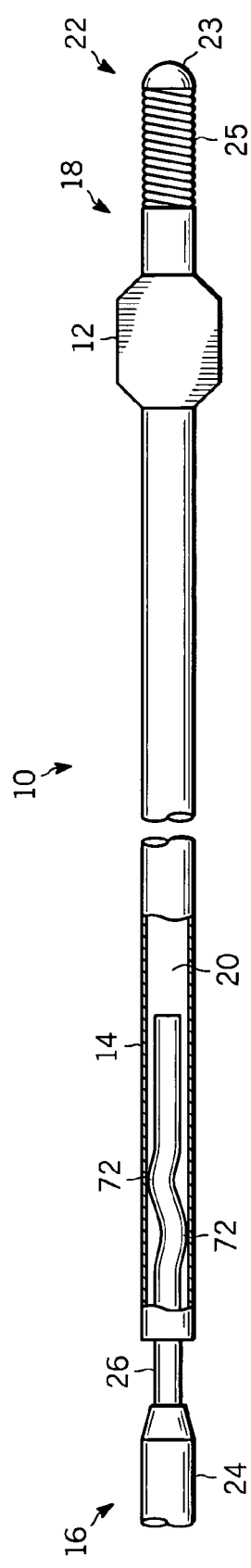

INTRALUMINAL GUIDEWIRE WITH HYDRAULICALLY COLLAPSIBLE SELF-EXPANDING PROTECTION DEVICE

CROSS-REFERENCES TO RELATED APPLICATIONS

This is a continuation-in-part of U.S. patent application Ser. No. 10/295,153, filed Nov. 14, 2002, now abandoned entitled "Intraluminal Catheter with Hydraulically Collapsible Self-Expanding Protection Device" and assigned to the assignee of the present invention.

TECHNICAL FIELD

This invention relates generally to medical devices, and more particularly, to an intraluminal hydraulic guidewire apparatus for activating a distally located device such as an emboli containment filter for capturing embolic material in a blood vessel during a transluminal medical treatment.

BACKGROUND OF THE INVENTION

Stenotic lesions may comprise a hard, calcified substance or a softer thrombus material, each of which forms on the lumen walls of a blood vessel and restricts blood flow therethrough. Intraluminal treatments such as balloon angioplasty, stent deployment, atherectomy, and thrombectomy are well known and have been proven effective in the treatment of such stenotic lesions. These treatments often involve the insertion of a therapy catheter along a guidewire that was previously inserted into a patient's vasculature.

Balloon angioplasty is a treatment wherein a stenosis is deformed to reduce restriction and improve blood flow. A balloon catheter is inserted along the guidewire until the balloon is properly positioned at a target lesion. The balloon is then expanded to expand the stenosis. When this portion of the procedure is complete, the balloon is caused to collapse, and the catheter is removed along the guidewire. If appropriate, a stent carrying catheter may also be introduced into the patient's vasculature along the same guidewire. When properly positioned, the stent is expanded and serves as a scaffolding to maintain the blood vessel open and improve blood flow. After the stent is deployed, the stent catheter is backed out of the vessel along the guidewire. During a thrombectomy or atherectomy, a stenosis is mechanically cut or abraded away from the blood vessel walls. It is also known to utilize radio frequency signals and lasers to ablate a stenosis.

One concern associated with each of the above-described methods for treating stenotic lesions relates to the creation of stenotic debris or emboli which may then be carried by blood flow within the lumen of a blood vessel and subsequently enter various arterial vessels of the brain, lungs, etc., possibly causing significant damage. Thus, there have developed several procedures for dealing with stenotic debris or fragments.

One such known technique involves cutting the debris into small pieces, in the order of the size of a single blood cell. This process, however, is difficult to control and sometimes results in the accidental severing of larger fragments which may occlude the vasculature. Another known approach involves the use of suction to remove the embolic material. This process is likewise difficult to control because if the vacuum is too low, all the severed pieces may not be retrieved, and if the vacuum is too high, the vasculature may collapse.

Another known technique for capturing embolic material involves the use of a filter positioned distal to the stenosis for catching the fragments and removing them with a capturing device when the procedure is complete. For example, a filter (e.g. a self expanding nitinol filter) can be deployed on the distal portion of a guidewire, which is then inserted into a patient's vasculature and positioned downstream of the stenosis to be treated. A treatment catheter may then be inserted over or alongside the guidewire as previously described. It is necessary to collapse the filter during insertion and removal. After the filter is properly positioned, the filter is permitted to expand. It is known to provide a mechanical actuator such as a push-rod, which in turn is mechanically acted upon by a tube over the guidewire to collapse the filter. That is, when the tube urges the push-rod forward, the filter is mechanically collapsed. Such mechanical actuator mechanisms, unfortunately, raise certain concerns. For example, it may be difficult to negotiate the tube/push-rod assembly through torturous vasculature that may include tight curves resulting in difficulties when inserting or retracting the filter. Furthermore, difficulties may arise when it is necessary to permit the push-rod to retreat so as to allow the filter to expand to its full open position. Breakage of the tube or push-rod can occur which in turn may result in serious complications.

In order to minimize the concerns associated with mechanically actuated filters, it is known to employ fluid pressure to deploy a filter for capturing embolic material in a blood vessel during a transluminal medical treatment. For example, U.S. Pat. No. 5,814,064 issued Sep. 29, 1998 and entitled "Distal Protection Device", the teachings of which are hereby incorporated by reference, discloses an apparatus comprising a guidewire having a lumen therethrough and an expandable member coupled to a distal portion of the guidewire. The expandable member is in fluid communication with the lumen of the guidewire and is configured to receive fluid therethrough to expand radially outward relative to the guidewire. The expandable member is collapsed radially inward when the fluid pressure is removed. An emboli capturing device or filter is coupled to the expandable member and deploys radially outward relative to the guidewire upon expansion of the expandable member.

This system, however, gives rise to an additional concern. To function properly, the filter must contain a uniform number of pores or openings therethrough, each opening being of a specific size (e.g. 100 microns). Not only is it necessary to produce a mesh containing pores of the right size and number, but it is also necessary that the filter as a whole be of a size which is appropriately accommodated by the vessel in which it will be deployed. If the filter is of the type which is biased to be normally closed, it is difficult to assure that the correct pore size and filter diameter are achieved. In contrast, if the filter is biased to be normally open or expanded, it can be safely assumed that the filter, when deployed in a blood vessel, has the same pore size and diameter when it opens as it did when it was created. That is, the filter can more predictably permit blood to flow therethrough while still effectively capturing the stenotic fragments.

An additional problem associated with systems employing filters that are hydraulically biased normally closed centers around the requirement that pressure must be applied during the entire time that the filter is deployed. That is, to avoid unwanted or premature closure of the filter, the proximal end of the guidewire must be coupled to a source of fluid pressure or be capable of retaining fluid pressure during substantially the entire intraluminal procedure which could result in unwanted leakage. Furthermore, it would be difficult to switch therapy catheters (i.e. replacing a balloon catheter with a stent catheter as described above) while at the same time maintaining a constant source of pressure.

In view of the foregoing, it should be appreciated that it would be desirable to provide an intraluminal guidewire equipped with a hydraulically collapsible, self-expanding filter which provides predictable capture of emboli while at the same time overcoming the concerns associated with mechanical or hydraulically operated filter actuators.

SUMMARY OF THE INVENTION

According to an aspect of the invention there is provided an intraluminal guidewire system, comprising a first tubular member having a proximal end and a distal end and having a fluid containing lumen therethrough. A medical device is coupled to the first tubular member proximate its distal end. A slave actuating member is coupled to the medical device and is slidably mounted proximate the distal end for longitudinal movement with respect to the first tubular member. A master actuating member is configured for longitudinal movement within the first tubular member proximate the proximal end. The master actuating member is hydraulically coupled to the slave actuating member.

According to a further aspect of the invention there is provided a guidewire apparatus comprising a first tubular member having a proximal end and a distal end and having a fluid containing lumen therethrough. A slave actuating member is slidably mounted proximate the distal end for longitudinal movement with respect to the first tubular member. A master actuating member is configured for longitudinal movement within the first tubular member proximate the proximal end. The master actuating member is hydraulically coupled to the slave actuating member.

According to a still further aspect of the invention there is provided an intraluminal guidewire system, comprising a first tubular member having a proximal end and a distal end and having a fluid containing lumen therethrough. A medical device is coupled to the first tubular member proximate the distal end. A master actuating member is telescopically mounted within the lumen proximate the proximal end and is configured for longitudinal movement therein. A slave actuating member is telescopically mounted within the lumen proximate the distal end and is configured for longitudinal movement therein. The slave actuating member is coupled to the medical device and is hydraulically coupled to the master actuating member.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed description. The present invention will hereinafter be described in conjunction with the appended drawings, wherein like numerals denote like elements, and;

FIG. 1 illustrates a guidewire having an intraluminal, self-expanding protection device proximate its distal end;

FIG. 2 is a cross-sectional view of an intraluminal emboli capturing apparatus having an expanded filter in accordance with a first embodiment of the present invention;

FIG. 5 is a cross-sectional view of an intraluminal emboli capturing apparatus having a filter in an expanded state in accordance with a second embodiment of the present invention;

FIG. 6 is a cross-sectional view of the apparatus shown in FIG. 5 having a filter in a collapsed state;

FIG. 8 illustrates a guidewire having an intraluminal, self-expanding protection device in accordance with another embodiment of the present invention; and FIG. 9 illustrates a guidewire having an intraluminal, self-expanding protection device in accordance with yet another embodiment of the present invention.

DETAILED DESCRIPTION OF EXEMPLARY EMBODIMENTS

Figure 3:
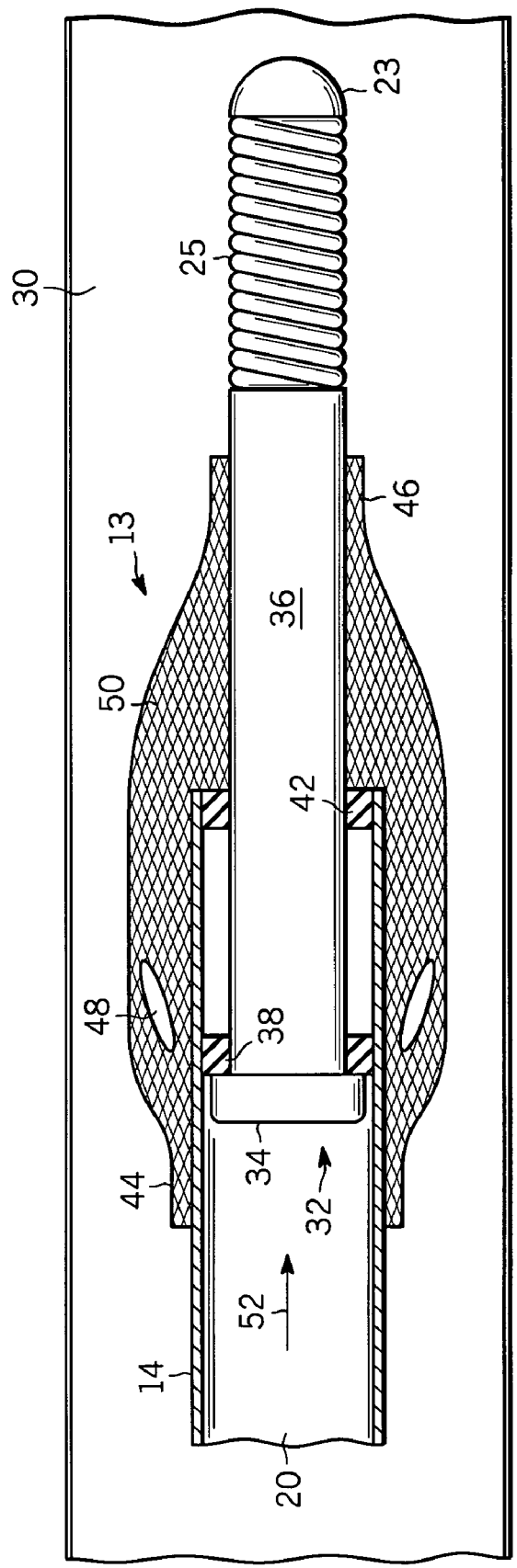
FIG. 3 is a cross-sectional view of the apparatus shown in FIG. 2 wherein the filter is shown in a collapsed state.

The following description is exemplary in nature and is not intended to limit the scope, applicability, or configuration of the invention in any way. Rather the following description provides a convenient illustration for implementing exemplary embodiments of the invention. Various changes to the described embodiments may be made in the function and arrangements of the elements described herein without departing from the scope of the invention.

Referring to FIG. 1, there is shown a guidewire 10 incorporating a low-profile, intraluminal, self-expanding protection device 12 (e.g. a filter, occluder, etc.) at its distal end. Guidewire 10 comprises a flexible tubular body, for example hypotube 14, having a proximal end 16 and a distal end 18. Hypotube 14 has a central lumen 20 extending therethrough and preferably has a generally circular cross-section with an outer diameter of, for example, 0.01 inches to 0.04 inches and a length of, for example, 120 to 320 centimeters. It should be appreciated, however, that lumen 20 may have a constant diameter or may be provided with a cross-section that is, for example, triangular, rectangular, oval, or any other desirable cross-section.

Hypotube member 14 may serve as a guidewire and therefore must be structurally suitable so as to permit guidewire 10 to be advanced through torturous vasculature to distal arterial locations without buckling or kinking. Thus, hypotube 14 may be made of stainless steel or polymeric materials such as polyamide, polyimide, polyethylene, etc. Preferably however, hypotube 14 is manufactured using an alloy of titanium and nickel generally referred to as nitinol, and which may be comprised of approximately 50% nickel and the remainder titanium. Nitinol hypotubes are found to have sufficient guidewire-like properties and high resistance to buckling. For further details, the interested reader is directed to U.S. Pat. No. 6,068,623 filed Mar. 6, 1997 and entitled "Hollow Medical Wires and Methods of Constructing Same" the teachings of which are hereby incorporated by reference.

The distal end of guidewire 10 is provided with an atraumatic, flexible and shapeable tip assembly 22 that comprises a tip 23 coupled to a coil 25 that is in turn coupled to distal end 18. For example, coil 25 may be attached to tip 23 and distal end 18 by any suitable method such as soldering, brazing, etc. Tip 23 and coil 25 may be made of, for example, stainless steel, or if desired, a radiopaque material such as an alloy of platinum to enable fluoroscopic monitoring of the tip assembly during an intravascular procedure. The proximal end of guidewire 10 may be provided with a valve and inflation assembly that comprises a sealing member 24 and a wire 26 which extends into the proximal portion of hypotube 14. A seal, not shown, is provided around wire 26 within the proximal portion of hypotube 14. As can be seen, the proximal portion of hypotube 14 is provided with an inflation port 28 that may be in turn coupled to a fluid inflation assembly 27 (e.g. a syringe). Inflation port 28 is in fluid communication with central lumen 20 in hypotube 14, thus providing an unrestricted fluid pathway between inflation port 28 and self-expanding protection device 12 for reasons to be further described below. Thus, by maneuvering member 24 and wire 26, the seal on wire 26 within the proximal portion of hypotube 14 either establishes or blocks the fluid pathway between inflation port 28 and distal end 18. For additional information regarding this inflation adapter, the interested reader is directed to U.S. Pat. No. 6,325,777 issued Dec. 4, 2001 and entitled "Low Profile Catheter Valve and Inflation Adapter". It should be understood, however, that other mechanisms are known for transmitting a fluid pressure to the distal end of hypotube 14 and would be suitable for use in conjunction with the present invention. The proximal end of hypotube 14 could, for example, simply be detachably coupled to a source of fluid pressure.

FIG. 2 is a cross-sectional view of an embolic filter deployed within a blood vessel 30. As can be seen, a plunger assembly 32 is positioned at and within the distal end of hypotube 14. Plunger 32 is configured for longitudinal or telescopic movement within hypotube 14, and comprises a proximal cap portion 34, an intermediate stem portion 36 attached to cap 34, and an atraumatic tip assembly 22 (described above) attached to the distal end of stem 36. Cap 34, stem 36 and tip 22 may be made from stainless steel or, if desired, cap 34 and stem 36 may be formed from another material such as nitinol. A first annular seal 38 is attached to cap 34 and/or stem 36 and is configured for movement along the interior surface of lumen 20 to deter fluid within lumen 20 from reaching the distal portion of hypotube 14; that is, region 40. If desired, a second annular seal 42 may be fixedly coupled to the interior surface of the distal end of lumen 20 for providing a seal between hypotube 14 and stem portion 36 of plunger 32. Seals 38 and 42 may be made of any suitable material such as rubber, silicone, etc. that possess adequate surface properties to function as a seal between stem 36 and the inter surface of hypotube 14. Alternatively, seals 38 and 42 may be made from an inelastic material and comprise, for example, a polyimide ring or bushing. Seals 38 and 42 can be slightly leaky without degrading performance of the inventive protection system, and seal 42 may primarily function to center plunger 32 within hypotube 14.

Figure 4:
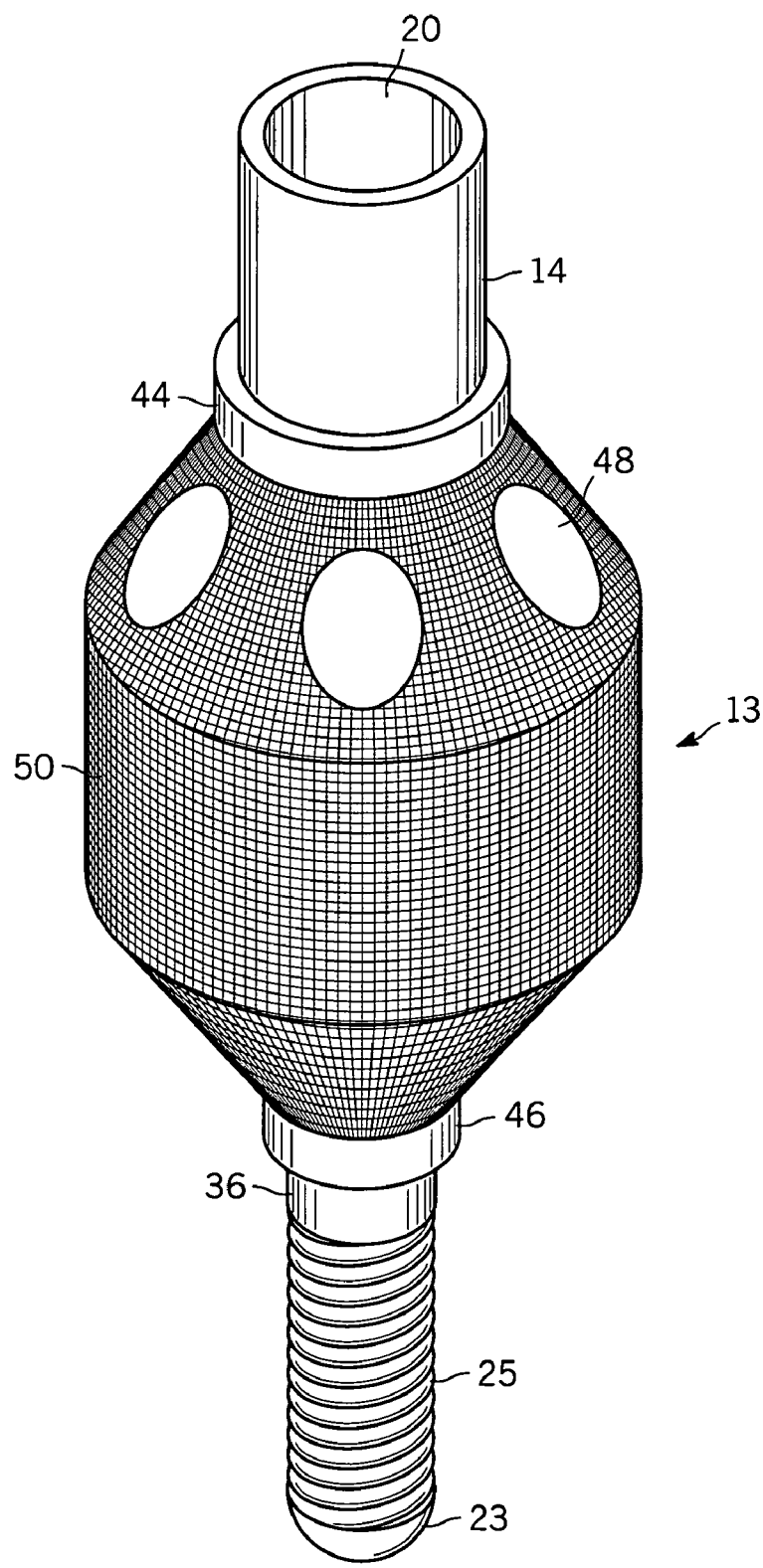
FIG. 4 is a isometric view of the apparatus shown in FIG. 2 and FIG. 3.

Self-expanding filter element 13 has an annular proximal portion 44 which is mechanically coupled or bonded to the outer surface of hypotube 14 and has a distal portion 46 which is mechanically coupled or bonded to stem 36 of plunger 32. Filter 13 is made of a resilient material having a memory such that it may be preset (for example, by heat treating) into a desired shape or configuration, and, after being distorted by some external force, will return to its preset shape when the external force is removed. Preferably, filter 13 is made of nitinol above-described. As can be seen, filter 13 includes a proximal region which includes a plurality of openings or holes 48 large enough to permit stenotic fragments or emboli to pass therethrough. The distal portion of filter 13 is comprised of a mesh 50 which captures the stenotic fragments passing into the filter through holes 48. Mesh 50 contains a plurality of micropores each having a diameter of, for example, approximately 100 microns. The shape and configuration of filter element 13 coupled to hypotube 14 and to stem member 36 and including holes 40 and mesh 50 is shown in isometric view in FIG. 4. However, it should be understood that the specific shape or configuration of filter 12 may vary. Furthermore, while filter 13 has been illustrated in FIGS. 2 and 3 as having a mesh distal portion, it should be appreciated that the entire filter may be comprised of a mesh as is shown in FIG. 4.

Referring again to FIG. 2, the diameter of filter 13 has been chosen to occupy substantially the entire cross-section of blood vessel 30 when in its preset or expanded configuration. In this manner, emboli or stenotic fragments originating upstream of filter 13 will enter holes 48 and be captured by mesh 50. However, during insertion into vessel 30 and removal therefrom when treatment is complete, it is necessary to urge filter 13 into its collapsed configuration as is shown in FIG. 3 wherein like referenced numerals denote like elements. This is accomplished as follows. Using an inflation adapter of the type described above, fluid pressure is applied to the proximal surface of cap 34 as is indicated by arrow 52. The fluid pressure causes plunger 32 to move in a distal direction. Since filter 13 has a proximal end coupled to hypotube 14 as is shown at 44 and has a distal end coupled to plunger 32 as is shown at 46, filter 13 is caused to collapse as is shown in FIG. 3. In this collapsed configuration, the mechanism may be removed from vessel 30 along with all stenotic fragments which have been captured in filter 13. Likewise, filter 13 is urged into the collapsed state shown in FIG. 3 when the filter is being inserted into the patient's vasculature. When the filter has been properly positioned, the fluid pressure indicated by arrow 52 is removed, and filter 13 returns to its preset shape such as is shown in FIG. 2 and FIG. 4.

FIG. 5 is a cross-sectional view of a second embodiment of the inventive intraluminal, collapsible, self-expanding filter assembly. Again, like elements are denoted with like referenced numerals. In the embodiment shown in FIG. 5, a second tubular member 54 (e.g. a hypotube) has a proximal portion which is positioned over a distal portion of hypotube 14 and is configured to slidingly move thereover in a telescopic fashion. A first annular seal 56 of the type above-described is attached to an inner surface of the proximal end of hypotube 54 and sealingly engages the outer surface of hypotube 14. A second annular seal 58 is fixedly attached to an outer surface of the distal end of hypotube 14 and sealingly engages the inner surface of hypotube 54. An atraumatic, flexible and shapeable tip assembly 22, of the type described above, is configured for attachment to the distal end of hypotube 54. Hypotubes 14 and 54 are preferably made of nitinol.

Once again, filter 13 has a proximal portion which is secured to the outer surface of hypotube 14 as is shown at 44. However, in this embodiment, distal portion 46 of filter 13 is secured to the outer surface of hypotube 54. Filter 13 is shown in FIG. 5 its preset self-expanding position within blood vessel 30 and thus occupies substantially the entire cross section of blood vessel 30. However, as previously described, during insertion of the filter into a patient's vasculature or when retracting the filter after the treatment has been completed, filter 13 must be collapsed. This is accomplished by applying a fluid pressure represented by arrow 62 to the inner surface of a tip 60 attached to hypotube 54 and coil 25 that in turn causes hypotube 54 to move in a distal direction. Since the distal end 46 of filter 13 is fixedly attached to an outer surface of hypotube 54, filter 13 will collapse as is shown in FIG. 6. As stated previously, the inventive assembly is inserted into, or removed from, a patient's vasculature in the collapsed position shown in FIG. 6. When the filter has been properly positioned in blood vessel 30, the fluid pressure is removed, and filter 13 once again returns to its original preset shape shown in FIG. 5.

Figure 7:
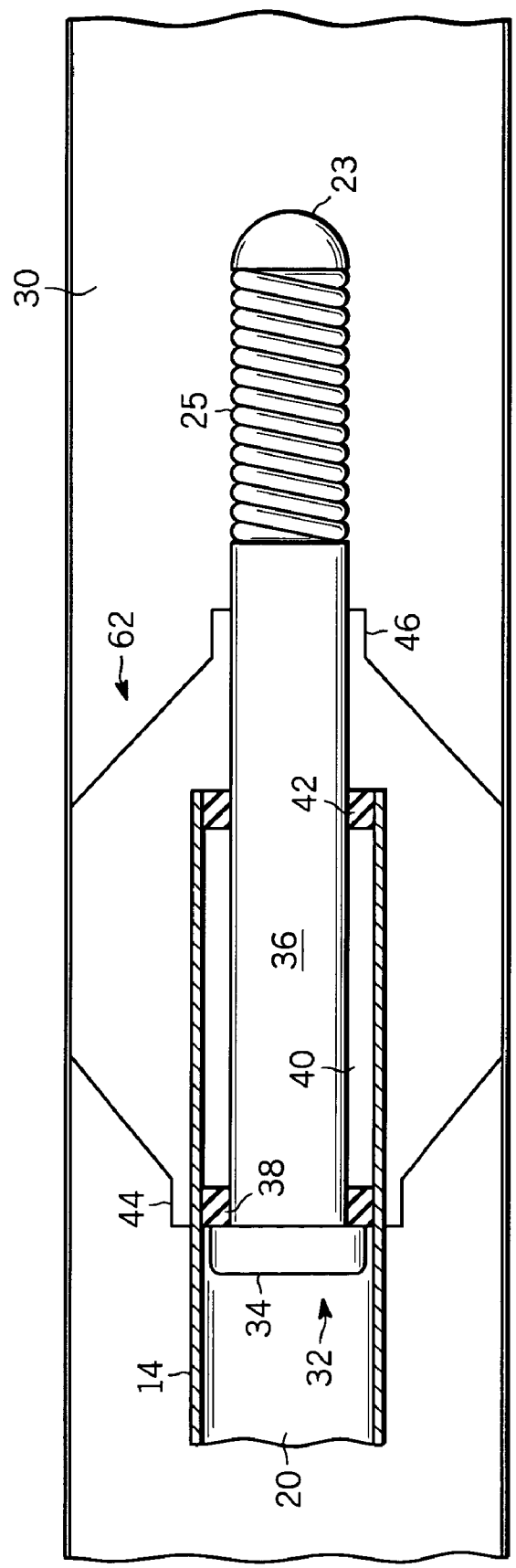
FIG. 7 is a cross-sectional view of an intraluminal emboli capturing apparatus having an expanded occluder in accordance with a still further embodiment of the present invention.

FIG. 7 is a cross-sectional view of a still further embodiment of the present invention. Again, like reference numerals denote like elements. As can be seen, the embodiment shown in FIG. 7 is similar to that shown in FIG. 2 except that filter 13 has been replaced by an occluder element 62 that may be a mesh coated with an elastomeric material that blocks the pores. As was the case with filter 13, occluder 62 is heat-set in a normally expanded configuration and is collapsed by the application of fluid pressure at the proximal end of plunger 32. However, instead of capturing emboli in a filter, the proximal portion of occluder 62 blocks emboli which result from an intravasculature procedure of the types described above. An aspiration catheter may then be inserted into the blood vessel over or alongside the guidewire to remove emboli that has been trapped by occluder 62. After the emboli has been removed, fluid pressure is applied to plunger 32 causing occluder 62 to collapse, thus enabling the removal of occluder 62.

FIG. 8 illustrates a guidewire having an intraluminal, self-expanding protection device in accordance with another embodiment of the present invention. In this embodiment, the fluid inflation assembly 27 including inflation port 28 shown in FIG. 1 is replaced by a proximal core segment 70 which may be an extension of wire 26 which extends into the proximal portion of hypotube 14 as is shown. Proximal core segment 70 acts as a master actuator or plunger which is telescopically movable within the lumen of hollow shaft of hypotube 14. If desired, proximal core segment 70 may be provided with crimps or bends 72 as is shown in FIG. 9. The degree to which proximal segment 70 is bent at 72 is selected such that proximal segment 70 forms an interference fit within lumen 20 to produce sufficient friction to hold segment 70 at a desired location within hypotube 20.

It should be appreciated that by urging master actuator 70 further into lumen 20, a fluid pressure is hydraulically transmitted to a slave actuator of device 12. That is, as the proximal core wire segment or master actuator 70 is pushed further into lumen 20, device 12 (e.g. a filter) is closed. As the master actuator is pulled back, a negative hydraulic pressure is produced causing the filter to open.

For example, if the hydraulic guidewire system shown in FIGS. 8 and 9 is employed in conjunction with the embodiment shown in FIG. 5, the hydraulically transmitted pressure produced when the proximal core segment or master actuator 70 is pushed further into hypotube 20 is applied to the proximal surface of cap 34 causing plunger 32 to move in a distal direction. Thus, proximal core segment 70 performs as a master cylinder, and plunger 32 in FIG. 5 performs as a slave cylinder. As stated previously, since filter 13 has a proximal end coupled to hypotube 14 as is shown at 44 in FIG. 2, and has a distal end coupled to plunger 32 as is shown at 46, filter 13 is caused to collapse and assume the position shown in FIG. 3. This may be accomplished by moving proximal core segment 70 into hypo tube 20 by only a few millimeters. When the filter has been properly positioned within the patient's vascular, the proximal core segment 70 may be retracted removing the pressure on plunger 32 and allowing filter 13 to return to its preset shape as is shown in FIG. 2.

In a similar fashion, the hydraulic actuating arrangement shown in FIGS. 8 and 9 may be used in conjunction with the embodiment shown in FIG. 5. In this case, hydraulic pressure which results from urging master actuator 70 into lumen 20 causes a hydraulic pressure to be applied to the inner surface of tip 60 attached to hypotube 54 and coil 25 as is shown in FIG. 5. This causes hypotube 54 to move in a distal direction. Since the distal end 46 of filter 13 is fixably attached to an outer surface of hypotube 54, filter 13 will collapse as is shown in FIG. 6. When master actuator segment 70 is retracted, the hydraulic pressure is removed, and filter 13 is allowed to return to its original preset shape shown in FIG. 5.

Thus, there has been provided an improved intraluminal guidewire equipped with a hydraulically actuated medical device. The device is inserted into a patient's vasculature in a collapsed state due to hydraulic pressure applied to the medical device. When the device is properly positioned, the hydraulic pressure is removed, and the device returns to its original shape.

In the foregoing specification, the invention has been described with reference to specific embodiments. However, it may be appreciated that various modifications can be made without departing from the scope of the invention as set forth in the appended claims. Accordingly, the specification and figures are to be regarded as illustrative rather than as restrictive, and all such modifications are intended to be included within the scope of the present invention.

The invention claimed is:

1. An intraluminal guidewire and distal protection device, comprising:
    an elongate hypotube having a proximal end and a distal end and having a fluid lumen therethrough, the hypotube having an outer diameter dimensioned to enable a therapeutic catheter to be advanced onto and along the guidewire;
    a distal protection device secured to the hypotube proximate said distal end, the protection device being deployable to an expanded configuration and being contractable about the hypotube after being deployed;
    a slave actuating member coupled to the distal protection device and slidably mounted proximate said distal end of the hypotube for longitudinal movement with respect to the hypotube; and
    a master actuating member having a portion disposed within the proximal portion of the lumen for longitudinal movement within said hypotube, whereby when the lumen is filled with fluid said master actuating member is hydraulically coupled to said slave actuating member.

2. A device according to claim 1 wherein said slave actuating member is configured for movement within said lumen.

3. A device according to claim 1 wherein said lumen has a constant diameter.

4. A device according to claim 1 wherein said master actuating member comprises a first plunger extending into the proximal end of the lumen.

5. A device according to claim 4 wherein said slave actuating member comprises a second plunger configured for telescopic movement within the lumen of the hypotube, said second plunger extending beyond the hypotube.

6. A device according to claim 4 wherein said slave actuating member comprises a second tubular member configured for telescopic movement with respect to the hypotube, said second tubular member extending over said distal end of the hypotube.

7. A device according to claim 1 wherein said distal protection device comprises an expandable filter for capturing emboli.

8. A device according to claim 1 wherein said distal protection device comprises an expandable occluder.

9. A device according to claim 5 further comprising a sealing member mounted to said second plunger for providing a fluid seal between the hypotube and said second plunger.

10. A device according to claim 6 further comprising a sealing member mounted to said second tubular member for providing a fluid seal between the hypotube and said second tubular member.

11. A device according to claim 7 wherein said filter comprises a proximal region having a plurality of openings therein of sufficient size for emboli to pass through.

12. A device according to claim 11 wherein said filter comprises a distal region having a plurality of pores therein of a size sufficiently small to capture the emboli.

13. A device according to claim 12 wherein at least said distal region is a mesh.

14. A guidewire apparatus comprising:
- an elongate hypotube having a proximal end and a distal end and having a fluid lumen therethrough, the hypotube having an outer diameter dimensioned to enable a therapeutic catheter to be advanced onto and along the guidewire;
- a self-expanding distal protection device disposed at the distal region of the hypotube and adapted to self-expand from a low profile configuration;
- a slave actuating member slidably mounted proximate said distal end for longitudinal movement with respect to the hypotube
- a master actuating member having a portion disposed within the proximal portion of the lumen for longitudinal movement within said hypotube, said master actuating member being hydraulically coupled to said slave actuating member through the hypotube lumen;
- the self-expanding distal protection device being coupled to the distal end of the hypotube and the slave actuating member so that actuation of the master actuating member will cause the distal protection device to be returned to its low profile configuration.

15. A device according to claim 14 wherein said slave actuating member is configured for movement within said lumen.

16. A device according to claim 14 wherein said lumen has a constant diameter.

17. A device accirding to claim 14 wherein said master actuating member comprises a first plunge.

18. A device according to claim 17 wherein said slave actuating member comprises a second plunger configured for telescopic movement within the hypotube, said second plunger extending beyond said distal end of the hypotube.

19. A device according to claim 17, wherein said slave actuating member comprises a second tubular member configured for telescopic movement with respect to the hypotube, said second tubular extending over said distal end of the hypotube.

20. A device according to claim 18 further comprising a sealing member fixedly attached to said second plunger for providing a fluid seal between said first tubular member and said second plunger.

21. A device according to claim 19 further comprising a sealing member fixedly attached to said second tubular member for providing a fluid seal between said first tubular member and said second tubular member.

22. An intraluminal guidewire and distal protection device, comprising:
- an elongate hypotube having a proximal end and a distal end and having a fluid lumen therethrough, the hypotube having an outer diameter dimensioned to enable a therapeutic catheter to be advanced onto and along the guidewire;
- a distal protection device secured to said hypotube proximate said distal end;
- a master actuating member telescopically mounted within said hypotube proximate said proximal end and configured for longitudinal movement therein; and
- a slave actuating member telescopically mounted within said lumen proximate said distal end and configured for longitudinal movement therein, said slave actuating member being coupled to said distal protection device and hydraulically coupled to said master actuating member;
- the distal protection device being self-expanding from a low profile and being coupled to the slave actuating member and hypotube so that operation of the master actuating member will cause the slave actuating member to move in a direction to collapse the distal protection device to its low profile.

23. A device according to claim 22 wherein said lumen has a constant diameter.

24. A device according to claim 22 wherein said master actuating member comprises a first plunger.

25. A device according to claim 24 wherein said slave actuating member comprises a second plunger extending beyond said distal end of said first tubular member.

26. A device according to claim 22 wherein said medical device comprises a filter for capturing emboli.

27. A device according to claim 22 wherein said medical device comprises an occluder.

28. A device according to claim 25 further comprising a sealing member fixedly attached to said second plunger for providing a fluid seal between said first tubular member and said second plunger.

29. A device according to claim 26 wherein said filter comprises a proximal region having a plurality of openings therein of sufficient size for emboli to pass through.

30. A device according to claim 29 wherein said filter comprises a distal region having a plurality of pores therein of a size sufficiently small to capture the emboli.

31. A device according to claim 30 wherein at least said distal region comprises a mesh.

* * * * *